US008870781B2

(12) United States Patent
Lee et al.

(10) Patent No.: US 8,870,781 B2
(45) Date of Patent: Oct. 28, 2014

(54) PRESSURE-PROVIDING INSTRUMENT AND BIOSIGNAL-MEASURING DEVICE INCLUDING A PRESSURE-PROVIDING INSTRUMENT

(75) Inventors: Jong Youn Lee, Yongin-si (KR); Kenichi Yamakoshi, Ishikawa Ken (JP); Kun Soo Shin, Seongnam-si (KR); Shinobu Tanaka, Kanazawa (JP); Takehiro Yamakoshi, Kanazawa (JP)

(73) Assignee: Samsung Electronics Co., Ltd., Suwon-Si (KR)

( * ) Notice: Subject to any disclaimer, the term of this patent is extended or adjusted under 35 U.S.C. 154(b) by 1950 days.

(21) Appl. No.: 11/896,770

(22) Filed: Sep. 5, 2007

(65) Prior Publication Data

US 2008/0058620 A1 Mar. 6, 2008

(30) Foreign Application Priority Data

Sep. 5, 2006 (KR) .................. 10-2006-0085116

(51) Int. Cl.
*A61B 5/02* (2006.01)
*A61B 17/00* (2006.01)
*A61B 5/021* (2006.01)
*A61B 5/022* (2006.01)
*A61B 5/1455* (2006.01)
*A61B 5/00* (2006.01)

(52) U.S. Cl.
CPC ............ *A61B 5/021* (2013.01); *A61B 5/02225* (2013.01); *A61B 5/14551* (2013.01); *A61B 5/681* (2013.01)
USPC ........... 600/485; 606/201; 600/490; 600/499

(58) Field of Classification Search
USPC ........... 600/485, 490, 499; 606/201, 203, 202
See application file for complete search history.

(56) References Cited

U.S. PATENT DOCUMENTS

| 4,307,727 | A | | 12/1981 | Haynes |
| 5,617,868 | A | * | 4/1997 | Harada et al. ............. 600/490 |
| 6,336,901 | B1 | | 1/2002 | Itonaga et al. |
| 6,443,906 | B1 | | 9/2002 | Ting et al. |
| 2001/0037068 | A1 | * | 11/2001 | Goto et al. ............. 600/485 |
| 2003/0208127 | A1 | * | 11/2003 | Archibald et al. ......... 600/494 |
| 2005/0288597 | A1 | * | 12/2005 | Kishimoto et al. ....... 600/499 |
| 2006/0079792 | A1 | | 4/2006 | Finburgh et al. |
| 2006/0253041 | A1 | * | 11/2006 | Shin et al. ............. 600/493 |

FOREIGN PATENT DOCUMENTS

| JP | 09-238910 | 9/1997 |
| JP | 2004-008240 | 1/2004 |
| JP | 2005-348904 | 12/2005 |
| JP | 2006-006450 | 1/2006 |
| KR | 10-2002-0080831 | 10/2002 |
| KR | 10-2006-0017515 | 2/2006 |

OTHER PUBLICATIONS

Japanese Office Action for corresponding Japanese Patent Application No. 2007-230649 dated Jul. 6, 2010.

(Continued)

*Primary Examiner* — Michael D'Angelo
*Assistant Examiner* — Christian Jang
(74) *Attorney, Agent, or Firm* — Staas & Halsey LLP

(57) ABSTRACT

A pressure supplier including an actuator that may be selectively expanded and contracted by applying a voltage, an elastic board being transformed in a predetermined direction to apply pressure upon a body part of a user when the actuator is contracted, and a guide member connecting with the actuator and the elastic board, and guiding the elastic board to be transformed in the predetermined direction while applying the pressure when the actuator is contracted.

22 Claims, 6 Drawing Sheets

(56) References Cited

OTHER PUBLICATIONS

Korean Office Action for corresponding Korean Patent Application No. 10-2006-0085116 dated Apr. 16, 2008, (1 pg).

* cited by examiner

PRESSURE-PROVIDING INSTRUMENT AND BIOSIGNAL-MEASURING DEVICE INCLUDING A PRESSURE-PROVIDING INSTRUMENT

CROSS-REFERENCE TO RELATED APPLICATIONS

This application claims the benefit of Korean Patent Application No. 10-2006-0085116, filed on Sep. 5, 2006, in the Korean Intellectual Property Office, the disclosure of which is incorporated herein by reference.

BACKGROUND

1. Field

One or more embodiments of the present invention relate to a pressure supplier for measuring a biosignal and a biosignal measurement device employing a pressure supplier, and more particularly, to a pressure supplier that can improve the portability of a biosignal measurement device and enhance user convenience by pressing only a radial artery area via an actuator and an elastic metallic plate, thereby measuring a user's biosignal.

2. Description of the Related Art

Ubiquitous-related technology may be applied to a myriad of fields in human life. In particular, Ubiquitous-HealthCare (hereinafter, U-HealthCare) has recently been in the spotlight as a notable technology area due to the "well-being" boom. U-HealthCare refers to Ubiquitous technology which enables anyone to readily receive medical services at any time and at any place by installing medical service-related chips or sensors in various places within the user's home. With U-HealthCare, various types of medical services, such as physical examinations, disease management, emergency care, consultation with a doctor and the like, which are currently performed only in hospitals, may be naturally integrated into our daily lives, and therefore may be accomplished without going to a hospital.

For example, a diabetic may wear a belt having a blood-sugar management system for blood-sugar management. A blood-sugar sensor attached to the belt may check the blood-sugar of the diabetic upon a specified event, and calculate the amount of required insulin corresponding thereto. When the blood-sugar of the diabetic becomes drastically low or high, the belt may provide the blood-sugar information to the diabetic's attending physician via a wireless network, and the attending physician may write out an optimal prescription or take necessary action for the medical emergency.

Also, because many diseases associated with the cardiovascular system are chronic diseases, patients may never completely recover and are therefore required to constantly remain vigilant of their health. Particularly, a person who once suffers from hypertension must take medication for the rest of his/her life. Also, hypertension may cause side effects, such as impotence, urinary incontinence, and the like. Therefore, in the case of diseases associated with the cardiovascular system, such as hypertension, taking prophylaxis before an attack is very important.

To prevent the onset of hypertension, a person is required to measure his/her normal blood pressure or pulse and check whether he/she has hypertension. A diagnostic method of hypertension before the onset of hypertension generally uses a method of measuring blood pressure and pulse and thereby measuring a baroreflex sensitivity, which is an index to indicate the condition of a cardiovascular system. Specifically, a user's susceptibility to cardiovascular system disease may be predicted by regularly measuring blood pressure and then by considering the fluctuation of the blood pressure.

Currently, a variety of portable blood pressure measurement devices have been developed and are used to measure blood pressure. Particularly, a blood pressure measurement device in the form of a wristwatch is widely used due to its portability. As an example, a portable pressure measurement device is constructed from a band-shaped air bag in the form of a wristwatch worn around the wrist. The portable blood pressure measurement device pressurizes the air bag using a mini-pump and measures a changing pulse waveform pattern via a pressure sensor. However, in the portable blood pressure measurement device constructed as above, when pressurizing the air bag, a user may feel strong pressure around the wrist and thus, feel some discomfort. In addition, the portability of the device is reduced due to the air bag.

Also, a blood pressure measurement device using a tonometry instrument is utilized. The blood pressure measurement device is in the form of a wristwatch where a sensor is provided between the muscle and the wrist bone, and measures the blood pressure by supplying a minimal amount of pressure to an artery of the wrist. Here, the pressure to be applied to the wrist may be reduced, but the sensor must be closely attached to the artery by injecting air from the outside. Thus, the user may not readily carry the blood pressure measurement device. Also, since the air bag and the sensor are comparatively large, an external pressure generator is required and thus, portability of the blood pressure measurement device may not be achieved.

Also, when a user presses a sensor and the pressure is transmitted to the radial artery, the radial artery becomes flat. Thus, a portable blood pressure measurement device both analyzing a pulse waveform, which incurs in the above-described situation, and measuring the blood pressure is utilized. It is advantageous in that a user can carry the portable blood pressure measurement device, but it is disadvantageous in that the user has to keep pressing the sensor by hand to generate the pressure. Also, the portable blood pressure measurement device is generally of a large size and thus, the user may not wear the portable blood pressure measurement device around the wrist.

As described above, a blood pressure measurement device according to the conventional art applies pressure around the wrist to measure a blood pressure. Thus, a user may be inconvenienced by having to repeatedly measure blood pressure using the blood pressure measurement device. Also, since the blood pressure measurement device is generally manufactured in a large size, the user may not readily wear the blood pressure measurement device. Accordingly, a portable biosignal measurement device which a user can readily carry at all times to accurately measure a biosignal, such as blood pressure, and the like, has been determined as desirable by the inventors of the present invention.

SUMMARY

One or more embodiments of the present invention provide a pressure supplier that can improve user convenience by applying pressure to only a radial artery area via an actuator and an elastic metallic plate, and thereby measuring a user's biosignal, and a biosignal measurement device employing the pressure supplier.

One or more embodiments of the present invention also provide a biosignal measurement device which a user can readily carry and can use to measure a biosignal since the size of the biosignal measurement device has been reduced by using only an actuator as a pressure unit to apply pressure to the wrist of the user.

Additional aspects and/or advantages will be set forth in part in the description which follows and, in part, will be apparent from the description, or may be learned by practice of the invention.

To achieve at least the above and/or other aspects and advantages, embodiments of the present invention include a pressure supplier including an actuator that may be selectively expanded and contracted by applying a voltage, an elastic board being transformed in a predetermined direction to apply pressure upon a body part of a user when the actuator is contracted, and a guide member connecting with the actuator and the elastic board, and guiding the elastic board to be transformed in the predetermined direction while applying the pressure when the actuator is contracted.

To achieve at least the above and/or other aspects and advantages, embodiments of the present invention include a biosignal measurement device including a bracelet membrane worn around a user's wrist, a pressure supplier, installed in the bracelet membrane, including a guide member connecting with an actuator and an elastic board, and guiding the elastic board to be transformed in a predetermined direction to apply pressure to the user's wrist when the actuator is contracted, and a sensor unit installed in the bracelet membrane, and measuring the user's biosignal from a radial artery of the wrist.

To achieve at least the above and/or other aspects and advantages, embodiments of the present invention include a biosignal measurement device including a bracelet membrane worn around a user's wrist, an actuator transformed towards the user's wrist to apply pressure to the wrist when a predetermined voltage is supplied, and a sensor unit installed in the bracelet membrane and measuring the user's biosignal from a radial artery of the wrist.

To achieve at least the above and/or other aspects and advantages, embodiments of the present invention include a pressure supplier including an actuator that may be selectively transformed in a predetermined direction to apply pressure upon a body part of a user by applying a voltage to the actuator, and a moving support to slide within a predetermined range when the actuator is contracting or expanding while maintaining a connection with a second end of the actuator at all times.

BRIEF DESCRIPTION OF THE DRAWINGS

These and/or other aspects and advantages will become apparent and more readily appreciated from the following description of embodiments, taken in conjunction with the accompanying drawings of which.

DETAILED DESCRIPTION OF EMBODIMENTS

Figure 1:
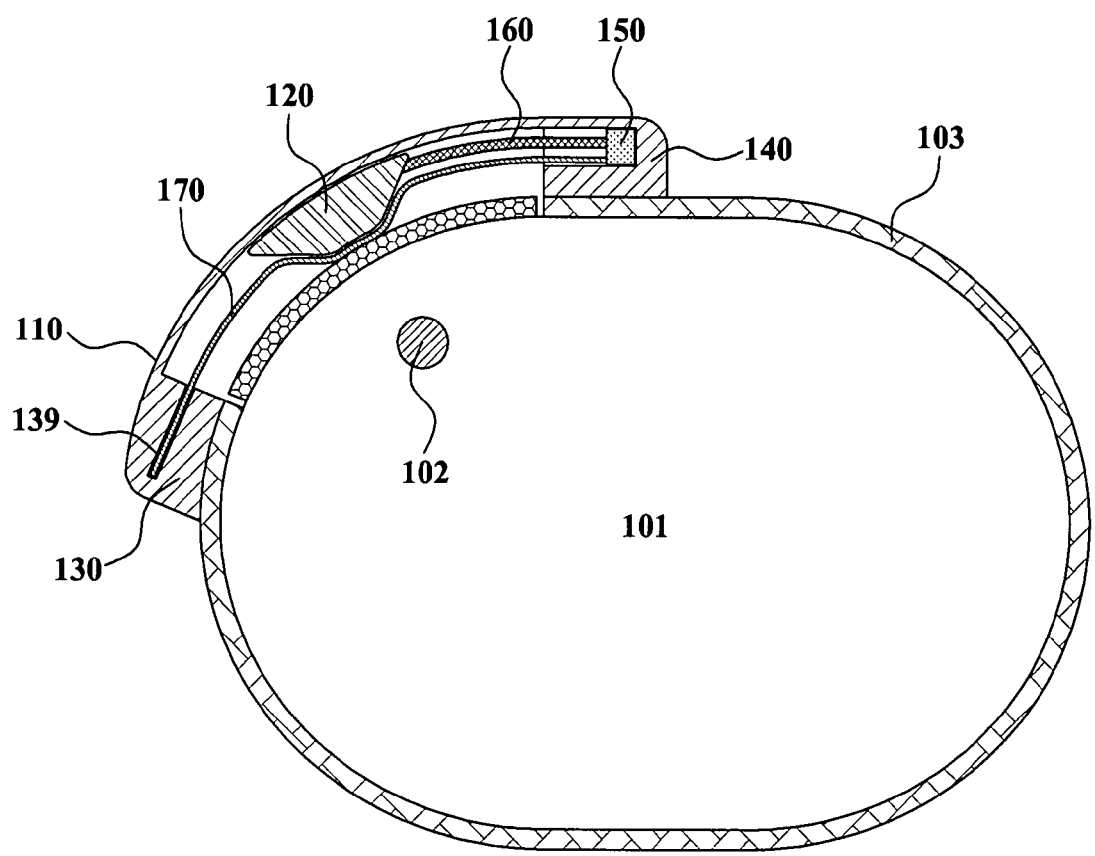
FIG. 1 illustrates a biosignal measurement device employing a pressure supplier, according to an embodiment of the present invention.

Reference will now be made in detail to embodiments, examples of which are illustrated in the accompanying drawings, wherein like reference numerals refer to the like elements throughout. Embodiments are described below to explain the present invention by referring to the figures.

A pressure supplier according to one or more embodiments of the present invention may be wearable around a body part of a user, e.g., a wrist, and may be included in a biosignal measurement device for measuring a biosignal. Here, the biosignal measurement device may take the form of an accessory that is wearable around the wrist, such as a wristwatch, a bracelet, and the like. Also, the biosignal measurement device may be take the form of an article such as a bracelet. As an example, the biosignal measurement device described herein may take the form of a bracelet, however, other forms are equally available including without limitation a hat, an anklet, and an armband.

The biosignal measurement device is also, for example, wearable around the wrist of the user, and may measure various types of biosignals, such as the user's pulse waveform, blood pressure, and the like. Here, an example in which the biosignal measurement device is wearable around the wrist of a user, measures the user's blood pressure, and a pressure supplier applies pressure to the wrist for measurement of the blood pressure will be described, however, other embodiments are equally available such as measuring a pulse rate using a cuff around an ankle and the like.

FIG. 1 illustrates a biosignal measurement device employing a pressure supplier, according to an embodiment of the present invention.

The biosignal measurement device according to an embodiment may include, for example, a bracelet membrane 103, a cover 110, a fixing support 120, a first side portion 140, a second side portion 130, a support 139, a sliding block 150, an actuator 160, and an elastic board 170.

Other elements of the biosignal measurement device, excluding the bracelet membrane 103, may be included in the pressure supplier according to an embodiment. The pressure supplier may include, for example, the cover 110, the fixing support 120, the first side portion 140, the second side portion 130, the support 139, the sliding block 150, the actuator 160, and the elastic board 170.

The bracelet membrane 103 may take the shape of a bracelet wearable around a wrist 101 of a user, for example. The size of the bracelet membrane 103 may be configured such that it may be worn around an adult's wrist. Here, the bracelet membrane 103 may be formed of an elastic material. Specifically, when the pressure supplier pressurizes the bracelet membrane 103, the bracelet membrane 103 may be transformed towards the wrist 101 to apply pressure to the radial artery 102 of the wrist 101. Also, when the pressure supplier terminates the applied pressure, the bracelet membrane 103 may be restored to its original shape.

In an embodiment, a guide member may include, for example, the cover 110, the fixing support 120, and the sliding block 150. The guide member may be connected with the actuator 160 and the elastic board 170. When the actuator 160 is contracted, the guide member may guide the elastic board 170 such that it is transformed towards the radial artery 102 to apply pressure to the radial artery 102.

The cover 110, one of the elements of the guide member, may be installed, e.g., on a side portion of the bracelet membrane 103. Specifically, the cover 110 may be provided on the side portion of the bracelet membrane 103 where the radial artery 102 of the wrist 101 is located, in order to apply pressure to the radial artery 102.

The fixing support 120, another element of the guide member, may be installed in an upper portion of the cover 110. Here, the fixing support 120 may be installed in the upper portion of the cover 110 so as to support the elastic board 170.

Also, the sliding block 150 may be installed on the side portion 140 of the cover 110 and thereby connect with the actuator 160 and the elastic board 170. When the actuator 160 is contracted, the sliding block 150 may slide towards the contraction direction to apply pressure to the elastic board 170. Specifically, since the actuator 160 connects with the fixing support 120 and the sliding board 150, the actuator 160 may pull the sliding block 150 when the actuator 160 is contracted.

Accordingly, when the actuator 160 is contracted, the sliding block 150 may slide towards the fixing support 120 corresponding to the contraction direction. As described above, when the sliding block 150 slides towards the fixing support 120, the sliding block 150 may apply pressure to the elastic board 170 in the direction of the fixing support 120.

When a predetermined voltage is supplied, the actuator 160 may be contracted or expanded. Specifically, the actuator 160 according to an embodiment may be a polymer actuator. Here, the actuator 160 may include a predetermined voltage supply unit (not illustrated) to supply a voltage for the contraction or expansion.

When the actuator 160 is contracted as described above, the elastic board 170 may be transformed towards a predetermined direction to apply pressure. Specifically, as described above, when the actuator 160 is contracted, the elastic board 170 may be bent towards a predetermined direction according to the pressure exerted by the sliding block 150. For the transformation, the elastic board 170 may be formed, e.g., of a predetermined metal plate having an elastic force, although the plate may be equally formed of other materials.

The elastic board 170 may be fixed to the second side portion 130 of the cover 110, and may connect with the sliding block 150. Here, when the sliding block 150 slides towards the fixing support 120, the elastic board 170 may receive pressure from the sliding block 150 and thus may be bent towards the wrist 101. Specifically, the elastic board 170 may connect with the fixing support 120 when the actuator 160 is not contracted. Thus, when the pressure is applied, the elastic board 170 may be transformed to be bent towards the wrist 101, in a direction opposite to the fixing support 170. An example of when the elastic board 170 may be bent towards the wrist 101 will be described with reference to FIG. 2.

Figure 2:
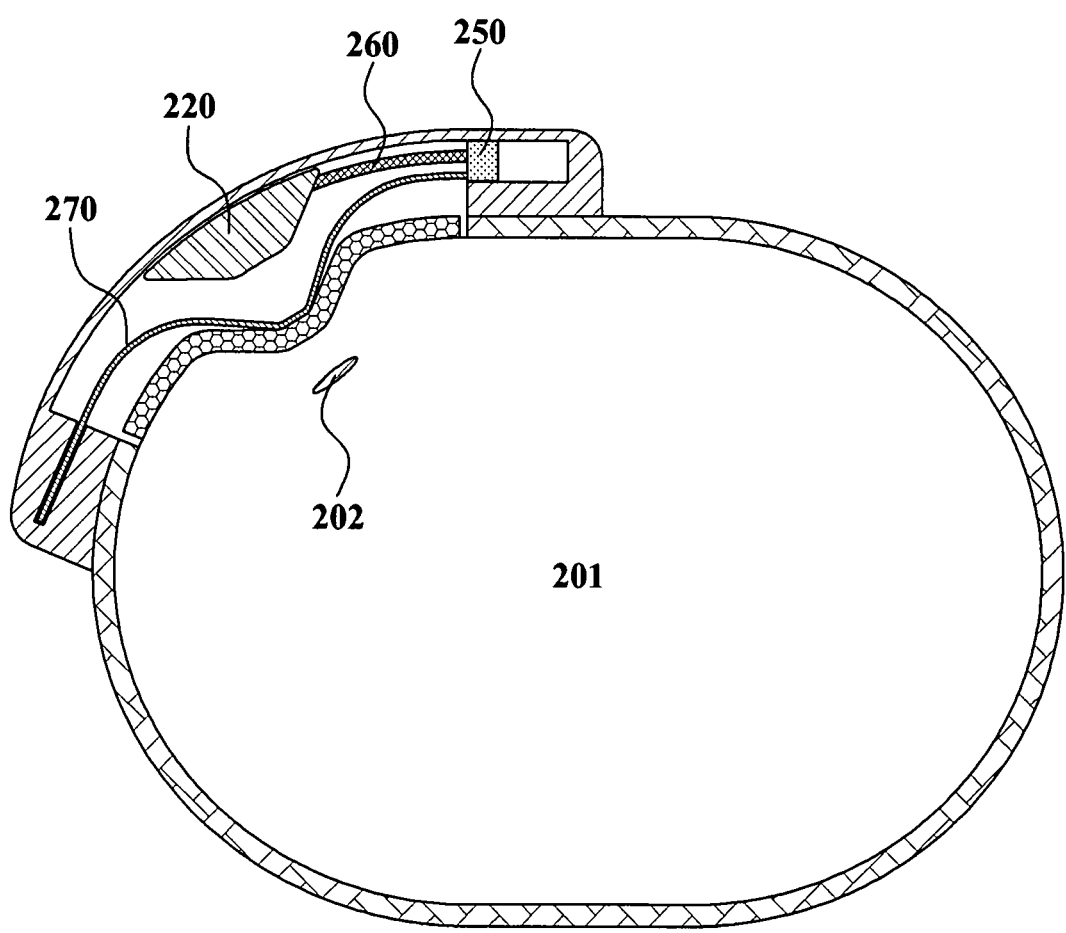
FIG. 2 illustrates a state in which a pressure supplier applies pressure to the wrist, according to an embodiment of the present invention.

FIG. 2 illustrates a pressure supplier applying pressure to the wrist, according to an embodiment of the present invention.

As described above with reference to FIG. 1, when an actuator 260 is contracted, a sliding block 250 may slide towards a fixing support 220 and thereby apply pressure to an elastic board 270. Here, the pressed elastic board 270 may be bent towards a wrist 201, which is an opposite direction to the fixing support 220, as shown in FIG. 2.

When the elastic board 270 is bent towards the wrist 201, the elastic board 270 may apply pressure to the radial artery 202 located in the wrist 201 of a user. Here, the pressure may increase in proportion to the size of the displacement of the sliding block 250. Specifically, when the sliding block 250 is moved maximally towards the fixing support 220, the amount of the pressure on the radial artery 202 may also reach a maximum.

When pressure is applied to the radial artery 202 as described above, the user's blood pressure may be measured. Specifically, when pressure is applied to the radial artery 202, a biosignal measurement device according to embodiments of the present invention may measure the blood pressure using, for example, an oscillometric method of measuring an oscillation of the radial artery 202, and thereby measuring the blood pressure described with reference to FIG. 3.

Figure 3:
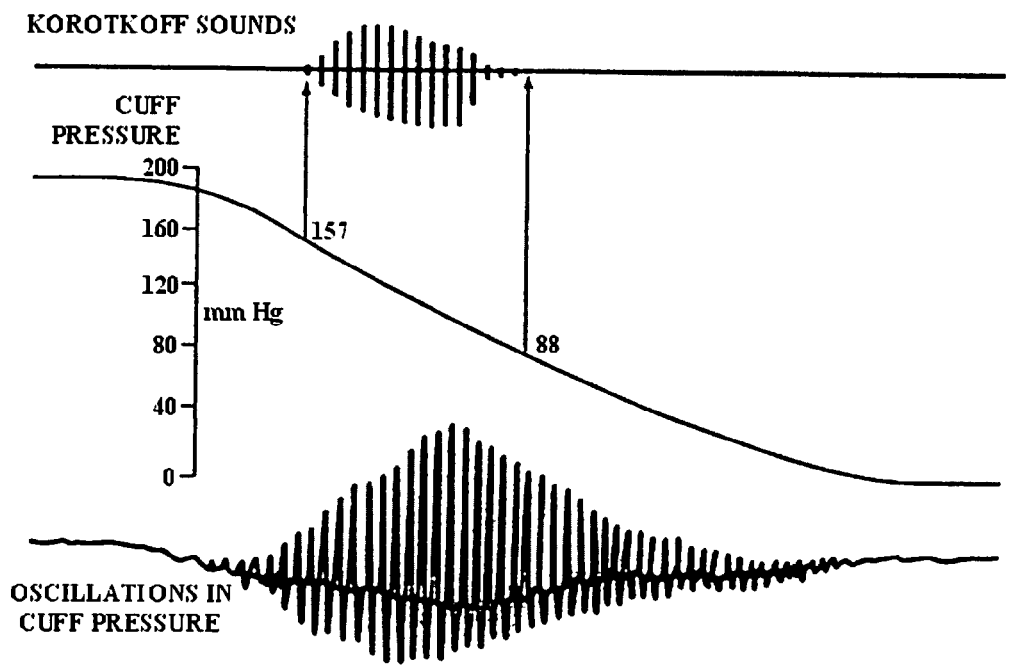
FIG. 3 illustrates an example of a characteristic ratio by an oscillometric method, according to an embodiment of the present invention.
Figure 3:
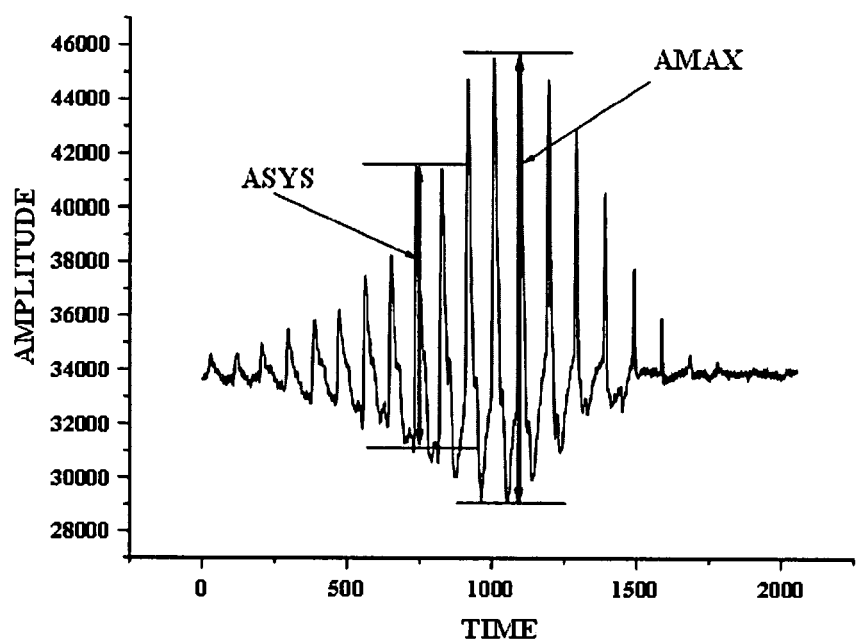

FIG. 3 illustrates an example of a characteristic ratio used by an oscillometric method of measuring a blood pressure, according to an embodiment of the present invention.

The top graph in FIG. 3 shows a comparison result between a reference method and an oscillometric method. The bottom graph shows an example of using a characteristic ratio according to the oscillometric method.

The reference method may apply pressure so that the pressure of a cuff surrounding a brachium is greater than the systolic blood pressure, and may measure the sound caused by blood flow during a decompression process, using a stethoscope. Specifically, the cuff pressure at a point in time when the sound is initially detected during the decompression process may be measured as the systolic blood pressure. The cuff pressure at a point in time when the sound disappears during the decompression process may be measured as a diastolic blood pressure.

The oscillometric method may use a procedure similar or identical to the reference method and measure an oscillation in a blood vessel during the procedure. Specifically, due to an arterial compliance characteristic, the oscillation in the blood vessel may reach a maximum when an intravascular pressure is equal to an extravascular pressure. Thus, the cuff pressure may be measured at a point in time corresponding to a certain ratio based on the amplitude of the maximum oscillation of the blood vessel. As shown in the bottom graph of FIG. 3, in the oscillometric method, the characteristic ratio may be set to Asys/Amax. The biosignal measurement device, according to the present invention may measure the blood pressure using the oscillometric method as described above.

Figure 4:
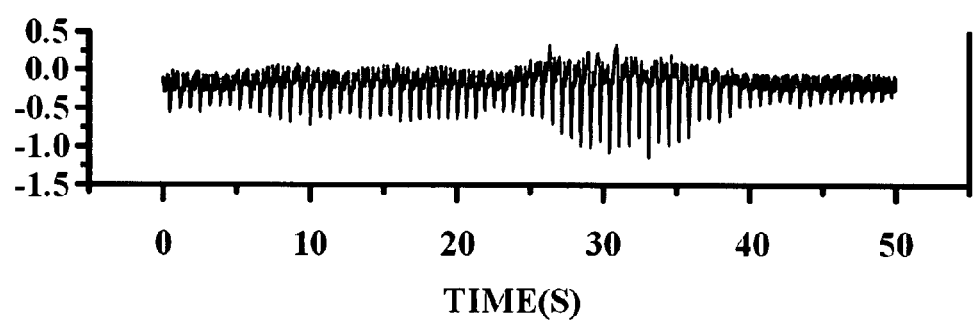
FIG. 4 illustrates results of measuring a blood pressure via a biosignal measurement device employing a pressure supplier, according to an embodiment of the present invention.

FIG. 4 illustrates results of measuring a blood pressure via a biosignal measurement device employing a pressure supplier, according to an embodiment of the present invention.

As shown in FIG. 4, as a result of measuring the blood pressure via the biosignal measurement device employing the pressure supplier according to an embodiment of the present invention, as the pressure applied to the radial artery increases, pulse waveform signals may show oscillometric waveforms. Here, the pulse waveform signals may be measured by a pressure sensor of the biosignal measurement device. Thus, the biosignal measurement device employing the pressure supplier according to an embodiment of the present invention may measure the user's blood pressure, e.g., via the above-described oscillometric method.

Referring again to FIG. 1, the biosignal measurement device according to an embodiment of the present invention may include a predetermined sensor unit (not illustrated) to measure the blood pressure as described above. The sensor unit may be installed in the bracelet membrane 103 and measure the user's biosignal from the radial artery 102 of the wrist 101.

The sensor unit may measure the user's biosignal from a point in time commencing when the elastic board 170 pressurizes the bracelet membrane 103 and thereby starts applying pressure to the wrist 101, to a point in time when the elastic board 170 is bent to a maximum amount and thereby the pressure also reaches a maximum amount.

Also, the sensor unit may measure the user's biosignal from a point in time when the elastic board 170 pressurizes the bracelet membrane 103 and thereby applies maximum pressure to the wrist 101 to a point in time when no more pressure is applied. Specifically, the sensor unit may measure the biosignal from a point in time when the elastic board 170 is maximally bent and thereby maximum pressure is applied to the wrist 101 to a point in time when the pressure is reduced and thereby the bent elastic board 170 is restored to an original shape.

As described above, the sensor unit, according to the present invention may measure the user's biosignal while applying pressure to the user's wrist and may also measure the user's biosignal while gradually reducing pressure from a point in time when the pressure is maximally applied.

Here, the sensor unit may include at least one sensor portion. Each sensor portion may include, for example, an optical sensor, a pressure sensor, and a luminous element. Also, the sensor unit may measure a pulse waveform from the radial artery 102 of the wrist 101, via the optical sensor. Also, the sensor unit may measure the user's blood pressure by measuring the pressure of the radial artery 102 via the pressure sensor. In addition, the sensor unit may measure an oxygen saturation level according to a light absorption difference between the user's oxyhemoglobin and reduced hemoglobin, using wavelengths of a red light band and an infrared band via the luminous element.

The biosignal measurement device according to an embodiment of the present invention may further include, for example, an information control unit and a communication module. The information control unit may generate biological information of the user using the user's measured biosignal. As an example, when the measured biosignal is represented as a numerical value which indicates the user's blood pressure, the information control unit may generate information about the numerical value, for example, biological information including information regarding whether the blood pressure reading is normal.

The communication module may transmit the measured biosignal or the biological information generated by the information control unit to a predetermined server or a terminal which is located in an external location. Specifically, the server may be constructed as a server installed in the user's personal computer (PC), a hospital server, and the like. Also, the terminal may be constructed as the user's mobile terminal, a mobile terminal of the user's family doctor, and the like.

As described above with reference to FIGS. 1 through 4, a pressure supplier according to an embodiment of the present invention may include, for example, an actuator, a sliding block, and an elastic board. Specifically, as the actuator is contracted, the sliding block may slide towards the direction of contraction. Also, as the sliding block moves in the direction of contraction, the elastic board may be bent towards a user's wrist. Also, as the elastic board is transformed, e.g., bent towards the user's wrist, the radial artery of the user's wrist may receive pressure from the elastic board.

Accordingly, a biosignal measurement device employing the pressure supplier according to an embodiment of the present invention may measure the user's blood pressure via, e.g., an oscillometric method, from a point in time when the radial artery starts receiving pressure from the elastic board, to a point in time when the elastic board is maximally transformed and thereby a maximum pressure is applied to the radial artery.

Also, as the contracted actuator is restored to an original shape, the sliding block may also be moved towards its original location and thus, the elastic board may gradually reduce the pressure applied to the radial artery of the user's wrist. Here, a biosignal measurement device employing the pressure supplier, according to an embodiment of the present invention, may measure the user's blood pressure via an oscillometric method from a point in time when the radial artery starts receiving a maximum amount of pressure to a point in time when the elastic board is restored to its original shape and thereby no significant pressure is applied to the radial artery.

Hereinafter, a biosignal measurement device according to another embodiment of the present invention will be described with reference to FIGS. 5 and 6.

Figure 5:
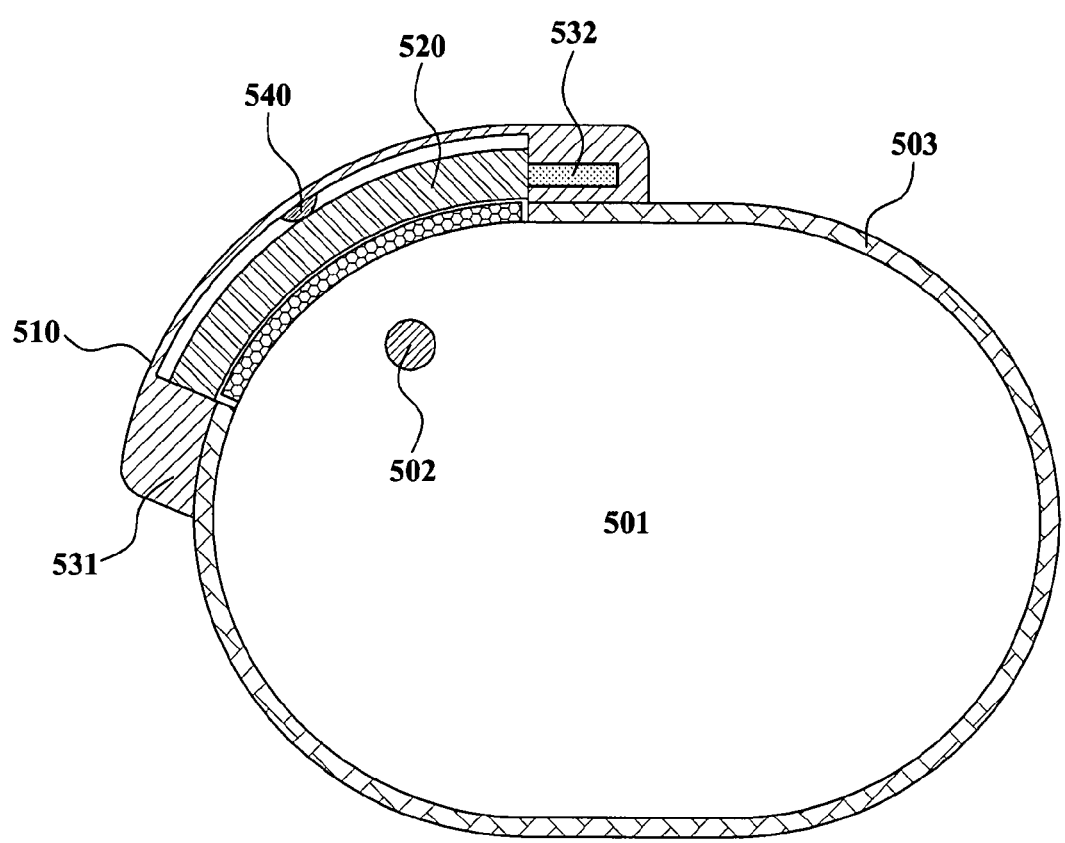
FIG. 5 illustrates a biosignal measurement device, according to an embodiment of the present invention.

FIG. 5 illustrates a biosignal measurement device, according to an embodiment of the present invention.

The biosignal measurement device including a pressure supplier according to an embodiment of the present invention may include, for example, a bracelet membrane 503, a cover 510, an actuator 520, a fixing support 531, a moving support 532, and an upper support 540.

Other elements of the biosignal measurement device, excluding the bracelet membrane 503, may be included in embodiments of the pressure supplier. Specifically, the pressure supplier may include, for example, a cover 510, an actuator 520, a fixing support 531, a moving support 532, and an upper support 540.

The bracelet membrane 503 may take the form of a bracelet which is wearable around a wrist 501 of a user. The size of the bracelet membrane 503 may be wearable around an adult's wrist. Here, the bracelet membrane 503 may be formed of an elastic material. Specifically, when the pressure supplier pressurizes the bracelet membrane 503, the bracelet membrane 503 may be transformed towards the wrist 501 to apply pressure to the radial artery 502 of the wrist 501. Also, when the pressure supplier terminates the applied pressure, the bracelet membrane 503 may be restored to its original shape.

The cover 510 may be installed on one side portion of the bracelet membrane 503. Specifically, the cover 510 may be installed on the side portion of the bracelet membrane 503 where the radial artery 502 is located, to apply pressure to the radial artery 502 of the wrist 501.

The upper support 540 may be installed on an upper portion of the cover 510. Specifically, the upper support 540 may be installed on the upper portion of the cover 510 and thereby support the actuator 520. Here, the upper support 540 may or may not be installed in the pressure supplier, depending upon the circumstances.

The actuator 520 may connect with the fixing support 531 and the moving support 532 of the cover 520. Here, the fixing support 531 may securely support the actuator 520, and the moving support 532 may movably support the actuator 520. Specifically, while the moving support 532 maintains a connection with the actuator 520 at all times, the moving support 532 may slide within a predetermined range when the actuator 520 is contracted or expanded.

When a predetermined voltage is supplied, the actuator 520 may be transformed towards the wrist 501 of the user and may apply pressure to the wrist 501. Specifically, the actuator 520 may be constructed to be transformed towards the wrist 501 while pulling the moving support 532, when the voltage is supplied. The transformation direction may be set by various methods of setting the transformation of an actuator, which are widely utilized in the art.

The actuator 520 may be constructed as any one of the widely-utilized actuators for the transformation. Particularly, the actuator 520, according to an embodiment of the present invention, may be constructed as a polymer actuator. For the transformation, the actuator 520 may include a predetermined voltage supply unit (not illustrated) for supplying the voltage.

The transformation of the actuator 520 towards the wrist 501 of the user will be described with reference to FIG. 6.

Figure 6:
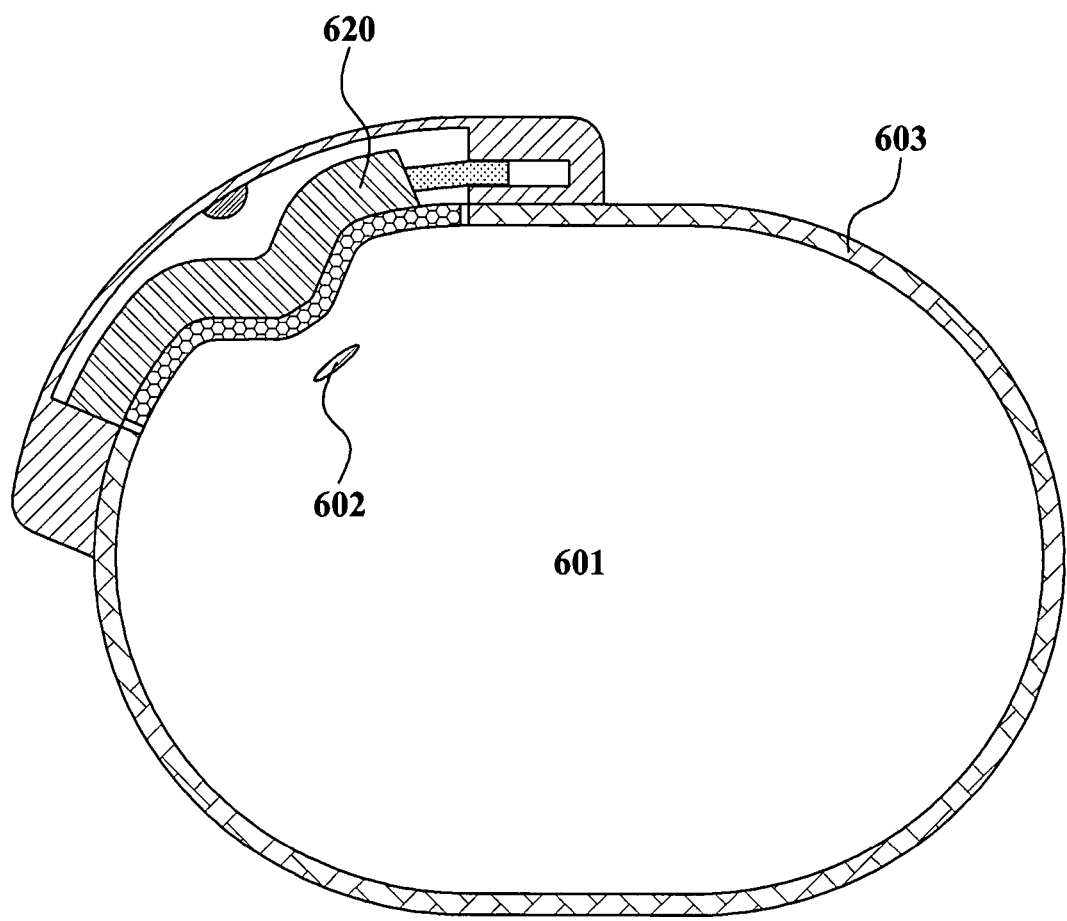
FIG. 6 illustrates a state in which a pressure supplier applies pressure to the wrist, according to an embodiment of the present invention.

FIG. 6 illustrates a pressure supplier applying pressure to a wrist, according to an embodiment of the present invention.

As shown in FIG. 6, when an actuator 620 is transformed towards a wrist 601 of a user, the actuator 620 may partially transform a contact portion along with a bracelet membrane 603 and thereby apply pressure to the wrist 601. Here, the pressure may increase in proportion to the amount of transformation of the actuator 620. Specifically, when the actuator 620 is maximally transformed towards the wrist 601, the pressure applied to a radial artery 602 also may reach a maximum.

As described above, when pressure is applied to the radial artery 602, the user's blood pressure may be measured. When the pressure is applied to the radial artery 602, a biosignal measurement device, according to an embodiment, may measure the user's blood pressure via, e.g., an oscillometric method of measuring an oscillation of the radial artery 602 and thereby measuring the user's blood pressure. The oscillometric method has been described with reference to FIGS. 3 and 4, and thus further detailed descriptions will be omitted.

Referring again to FIG. 5, the biosignal measurement device, according to an embodiment of the present invention may include a predetermined sensor unit (not illustrated) to measure the blood pressure as described above. The sensor unit may be installed in the bracelet membrane 503 and may measure the user's biosignal from the radial artery 502 of the wrist 501. The sensor unit may measure the biosignal from a point in time when the actuator 520 pressurizes the bracelet membrane 503 and thereby starts applying pressure to the wrist 501, to a point in time when the actuator 520 is maximally transformed and thereby the pressure also reaches a maximum amount.

Also, the sensor unit may measure the user's biosignal from a point in time when the actuator 520 pressurizes the bracelet membrane 503 and thereby applies maximum pressure to the wrist 501 to a point in time when the actuator 520 is restored to its original shape and thereby no more pressure is applied.

As described above, the sensor unit according to one or more embodiments of the present invention may measure the user's biosignal during the application of pressure to the user's wrist and may also measure the user's biosignal during a gradual reduction in pressure starting from a point in time when the pressure is maximally applied.

Here, the sensor unit may include at least one sensor portion. Each sensor portion may include, for example, an optical sensor, a pressure sensor, and a luminous element. Also, the sensor unit may measure a pulse waveform from the radial artery 502 of the wrist 501 via the optical sensor. Also, the sensor unit may measure the user's blood pressure by measuring the pressure of the radial artery 502 via the pressure sensor. In addition, the sensor unit may measure an oxygen saturation level according to a light absorption difference between the user's oxyhemoglobin and reduced hemoglobin using wavelengths of a red light band and an infrared band via the luminous element.

The biosignal measurement device according to an embodiment of the present invention may further include, for example, an information control unit and a communication module. The information control unit may generate biological information of the user from the user's measured biosignal. As an example, when the measured biosignal is represented as a numerical value which indicates the user's blood pressure, the information control unit may generate information about the numerical value, for example, biological information including information about whether the blood pressure reading is normal.

The communication module may transmit the measured biosignal or the biological information generated by the information control unit to a predetermined server or a terminal located in an external location. Specifically, the server may be constructed as a server that is installed in the user's PC, a hospital server, and the like. Also, the terminal may be constructed as the user's mobile terminal, a mobile terminal of the user's family doctor, and the like.

As described above, the biosignal measurement device according to embodiments of the present invention may apply pressure to the wrist of a user thereby measure the user's biosignal by transforming an actuator or an elastic board. Accordingly, the biosignal measurement device may be constructed with a comparatively simple design and may be highly portable. Also, user convenience may be improved by applying pressure to only a radial artery area, not the whole wrist, to measure the user's biosignal.

A pressure supplier, and a biosignal measurement device employing the pressure supplier according to embodiments of the present invention may enhance user convenience by pressing only a radial artery area via an actuator and an elastic metallic plate, thereby measuring a user's biosignal.

In addition, a biosignal measurement device according to embodiments of the present invention may reduce the size of the biosignal measurement device by using only an actuator to apply pressure to the wrist of the user. Therefore, a user may readily carry the biosignal measurement device to measure a biosignal.

Although a few embodiments have been shown and described, it would be appreciated by those skilled in the art that changes may be made in these embodiments without departing from the principles and spirit of the invention, the scope of which is defined in the claims and their equivalents.

What is claimed is:

1. A pressure supplier comprising:
   an actuator;
   an elastic board being transformed in a predetermined direction to apply pressure upon a body part of a user when the actuator is contracted; and
   a guide member connecting with the actuator and the elastic board, and guiding the elastic board to be transformed in the predetermined direction while applying the pressure when the actuator is contracted, wherein the guide member comprises a sliding block sliding towards a contraction direction to apply pressure to the elastic board when the actuator is contracted.

2. The pressure supplier of claim 1, wherein the pressure supplier is in a form of a cover and installed in a predetermined biosignal measurement device which is wearable around the user's wrist, and measures the user's biosignal.

3. The pressure supplier of claim 1, wherein the actuator is a polymer actuator.

4. A pressure supplier comprising:
   an actuator;
   an elastic board being transformed in a predetermined direction to apply pressure upon a body part of a user when the actuator is contracted; and
   a guide member connecting with the actuator and the elastic board, and guiding the elastic board to be transformed in the predetermined direction while applying the pressure when the actuator is contracted, wherein the guide member comprises
a sliding block sliding towards a contraction direction to apply pressure to the elastic board when the actuator is contracted.

5. The pressure supplier of claim 4, further comprising a cover comprising a side portion and an upper portion and wherein the fixing support is installed in the upper portion of the cover and the elastic board connects with the side portion of the cover and the sliding block, and maintains contact with the fixing support when the actuator is not contracted.

6. The pressure supplier of claim 5, wherein the elastic board is transformed towards a direction opposite from the fixing support according to the pressure exerted by the sliding block, when the actuator is contracted, and the opposite direction from the fixing support is a direction towards the wrist of the user.

7. A biosignal measurement device comprising:
a bracelet membrane capable of being worn around a user's wrist;
a pressure supplier, installed in the bracelet membrane, including a guide member connecting with an actuator and an elastic board, and guiding the elastic board to be transformed in a predetermined direction to apply pressure to the user's wrist when the actuator is contracted, wherein the guide member comprises a sliding block sliding towards a contraction direction to apply pressure to the elastic board when the actuator is contracted; and
a sensor unit installed in the bracelet membrane, and measuring the user's biosignal from a radial artery of the wrist.

8. The biosignal measurement device of claim 7, wherein the pressure supplier comprises:
a cover comprising a first side portion, a second side portion, and an upper portion;
a fixing support being installed in the upper portion of the cover;
the actuator connecting with the fixing support and the first side portion of the cover; and
the sliding block connecting with the actuator on the first side portion of the cover; and
the elastic board receiving pressure from the sliding block, and thereby being transformed towards the user's wrist to apply pressure to the wrist when the sliding block slides towards the contraction direction.

9. The biosignal measurement device of claim 8, wherein the actuator is a polymer actuator.

10. The biosignal measurement device of claim 7, wherein the sensor unit comprises:
at least one pulse waveform sensor measuring the user's pulse waveform from the radial artery; and
a pressure sensor measuring the user's blood pressure by measuring a pressure of the radial artery.

11. The biosignal measurement device of claim 7, wherein the sensor unit comprises:
at least two luminous elements emitting a red light and an infrared ray towards the wrist respectively, and measuring an oxygen saturation level.

12. The biosignal measurement device of claim 7, wherein the sensor unit measures the user's biosignal from a point in time when the pressure supplier starts applying pressure to the wrist to a point in time when the pressure supplier applies pressure to the wrist at a maximum amount.

13. The biosignal measurement device of claim 7, wherein the sensor unit measures the user's biosignal from a point in time when the pressure supplier applies pressure to the wrist at a maximum amount to a point in time when the pressure supplier does not apply pressure any longer.

14. The biosignal measurement device of claim 7, further comprising:
an information control unit generating biological information of the user from the measured biosignal; and
a communication module transmitting the biosignal or the biological information to a predetermined server or a terminal.

15. A biosignal measurement device comprising:
a bracelet membrane capable of being worn around a user's wrist;
an actuator adapted to contract when a predetermined voltage is supplied to the actuator;
an elastic element that is transformed towards the user's wrist to apply pressure to the wrist when the actuator is contracted;
a guide member connecting with the actuator and the elastic element and guiding the elastic element to be transformed toward the user's wrist, wherein the guide member comprises a sliding block sliding towards a contraction direction to apply pressure to the elastic board when the actuator is contracted; and
a sensor unit installed in the bracelet membrane and measuring the user's biosignal from a radial artery of the wrist.

16. The biosignal measurement device of claim 15, wherein the sensor unit comprises:
at least one pulse waveform sensor measuring the user's pulse waveform from the radial artery; and
a pressure sensor measuring the user's blood pressure by measuring a pressure of the radial artery.

17. The biosignal measurement device of claim 15, wherein the sensor unit comprises:
at least two luminous elements emitting a red light and an infrared ray towards the wrist respectively, and measuring an oxygen saturation level.

18. The biosignal measurement device of claim 15, wherein the sensor unit measures the user's biosignal from a point in time when the pressure supplier starts applying pressure to the wrist to a point in time when the pressure supplier applying pressure to the wrist at a maximum amount.

19. The biosignal measurement device of claim 15, wherein the sensor unit measures the user's biosignal from a point in time when the pressure supplier applies pressure to the wrist at a maximum amount to a point in time when the pressure supplier does not apply pressure any longer.

20. The biosignal measurement device of claim 15, further comprising:
an information control unit generating biological information of the user from the measured biosignal; and
a communication module transmitting the biosignal or the biological information to a predetermined server or a terminal.

21. The biosignal measurement device of claim 15, wherein the actuator is a polymer actuator.

22. The biosignal measurement device of claim 15, further comprising:
a fixing support to securely support the actuator at a first end; and
the sliding block, which slides within a predetermined range when the actuator is contracting or expanding while maintaining a connection with a second end of the actuator at all times.

* * * * *